(12) United States Patent
Fortuna (10) Patent No.: US 7,040,322 B2
(45) Date of Patent: May 9, 2006

(54) COMBINATION ARTIFICIAL AIRWAY DEVICE AND ESOPHAGEAL OBTURATOR

(76) Inventor: Anibal de Oliveira Fortuna, Rua Gal Rondon 42, 11030-570 Santos, SP (BR)

( * ) Notice: Subject to any disclaimer, the term of this patent is extended or adjusted under 35 U.S.C. 154(b) by 497 days.

(21) Appl. No.: 10/289,655

(22) Filed: Nov. 7, 2002

(65) Prior Publication Data

US 2004/0020491 A1    Feb. 5, 2004

Related U.S. Application Data

(60) Provisional application No. 60/339,092, filed on Nov. 8, 2001.

(51) Int. Cl.
*A61M 16/00* (2006.01)
(52) U.S. Cl. ............... 128/207.15; 128/207.14; 128/200.24; 604/97.03; 604/101.01; 604/103.07
(58) Field of Classification Search .......... 128/200.24; 128/207.14–207.18; 604/97.01–101.01; 606/190–200; 600/204, 207, 210
See application file for complete search history.

(56) References Cited

U.S. PATENT DOCUMENTS

| 4,016,885 | A | * | 4/1977 | Bruner ............... 604/100.01 |
| 4,334,534 | A | | 6/1982 | Ozaki |
| 4,497,318 | A | | 2/1985 | Donmichael |
| 4,509,514 | A | | 4/1985 | Brain |
| 4,976,261 | A | * | 12/1990 | Gluck et al. ............ 128/207.15 |
| 4,995,388 | A | | 2/1991 | Brain |
| 5,241,956 | A | | 9/1993 | Brain |
| 5,249,571 | A | | 10/1993 | Brain |
| 5,297,547 | A | | 3/1994 | Brain |
| 5,303,697 | A | | 4/1994 | Brain |
| 5,305,743 | A | | 4/1994 | Brain |
| 5,355,879 | A | | 10/1994 | Brain |
| 5,391,248 | A | | 2/1995 | Brain |
| 5,443,063 | A | | 8/1995 | Greenberg |
| 5,499,625 | A | | 3/1996 | Frass et al. |
| 5,584,290 | A | | 12/1996 | Brain |
| 5,632,271 | A | | 5/1997 | Brain |
| 5,682,880 | A | | 11/1997 | Brain |
| 5,711,293 | A | | 1/1998 | Brain |
| 5,746,202 | A | | 5/1998 | Pagan |
| 5,771,889 | A | | 6/1998 | Pagan |
| 5,791,341 | A | | 8/1998 | Bullard |
| 5,819,733 | A | * | 10/1998 | Bertram ............... 128/207.15 |
| 5,878,745 | A | | 3/1999 | Brain |
| 5,896,858 | A | | 4/1999 | Brain |
| 5,937,860 | A | | 8/1999 | Cook |
| 5,979,445 | A | | 11/1999 | Neame et al. |
| 5,983,897 | A | | 11/1999 | Pagan |

(Continued)

FOREIGN PATENT DOCUMENTS

GB    2205499    6/1987

(Continued)

*Primary Examiner*—Glenn K. Dawson
(74) *Attorney, Agent, or Firm*—Reising, Ethington, Barnes, Kisselle, P.C.

(57) ABSTRACT

A combination artificial airway device and esophageal obturator (10) includes a esophageal cuff (16) and supraglottic cuff (14) that are inflated in a sequence to provide quick isolation of the esophagus relative to the tracheal air passage. The supraglottic cuff is asymmetrical in shape with a wedge like or cone like shape that is ergonomically shaped for providing less trauma to the pharyngeal tissues. A pressure indicator (25) surrounds a pilot balloon (28) for continuous monitoring of the internal pressure within the cuffs (14 & 16).

20 Claims, 5 Drawing Sheets

U.S. PATENT DOCUMENTS

| | | |
|---|---|---|
| 5,988,167 A | 11/1999 | Kamen |
| 6,003,514 A | 12/1999 | Pagan |
| 6,012,452 A | 1/2000 | Pagan |
| 6,021,779 A | 2/2000 | Pagan |
| 6,050,264 A | 4/2000 | Greenfield |
| 6,070,581 A | 6/2000 | Augustine et al. |
| D429,811 S | 8/2000 | Bermudez |
| 6,095,144 A | 8/2000 | Pagan |
| 6,116,243 A | 9/2000 | Pagan |
| 6,119,695 A | 9/2000 | Augustine et al. |
| 6,439,232 B1 | 8/2002 | Brain |

FOREIGN PATENT DOCUMENTS

| | | | | |
|---|---|---|---|---|
| GB | 2205499 | * | 12/1988 | ............ 128/207.15 |
| WO | 01/24860 | * | 4/2001 | ............ 128/207.15 |
| WO | WO 01/24860 A2 | | 4/2001 | |

* cited by examiner

COMBINATION ARTIFICIAL AIRWAY DEVICE AND ESOPHAGEAL OBTURATOR

RELATED APPLICATIONS

This application is a continuation-in-part of U.S. Provisional Application 60/339,092 filed on Nov. 8, 2001.

TECHNICAL FIELD

The field of this invention relates to medical device in the form of a supraglottic mask airway which facilitates lung ventilation in an unconscious patient and prevents upper airway obstruction, besides providing an immediate evacuation pathway to any gastric-esophageal content.

BACKGROUND OF THE DISCLOSURE

Endotracheal tubes have long been accepted to establish a direct path from the trachea to the ambient exterior or to a ventilation machine. However, endotracheal intubation requires a high degree of skill and the use of supporting medical devices such as a laryngoscope for visualization of the glottis. Furthermore, an endotracheal tube passes into and adjacent the larynx which poses a potential for serious damage to this important speech organ. Accidental insertion into the esophagus can also occur.

Supraglottic masks which do not intrude into the trachea and avoid the known problems of endotracheal tubes. Laryngeal masks, as a supraglottic device, have become accepted alternative to avoid the need of sealing within the trachea or the accidental insertion of the endotracheal tube into the esophagus.

Early versions of alternatives to endotracheal tubes used inflatable cuffs but needed an exterior face mask placed over the face of the patient to stop air leakage while the patient is being ventilated via the air ports.

One widely accepted laryngeal mask device is disclosed in U.S. Pat. No. 4,509,514 to Archibald Brain. This artificial airway device is in the form of a laryngeal mask airway. This laryngeal mask airway comprises of a tube opening into the interior of a mask portion. The periphery of the mask may be inflatable and provides a seal around the inlet of the larynx.

A disadvantage related with the use of this traditional laryngeal mask device is encountered in patients who are at risk from vomiting or regurgitating stomach contents while unconscious. Although the device is known to form a seal around the laryngeal inlet sufficient to permit artificial ventilation of the lungs, this seal may be sometimes insufficient to prevent lung contamination during retching, vomiting or regurgitation. Besides, the bulk size of these devices may impede, or create difficulties to the prompt access to the esophagus for the passage of an oral or nasal gastric tube to drain eventual esophageal/stomach contents. Due also to its design, it is possible that when a certain ventilation pressure is reached or when the device is not properly placed, a leak of gases from the repetitive ventilation attempts may reach and enter the esophagus, inflating the stomach increasing the risk of regurgitation and discharge of its contents.

In order to minimize these serious problems, modifications were proposed and introduced on these laryngeal mask ventilation devices to provide a sort of gastric drainage as disclosed in U.S. Pat. Nos. 5,241,956 and 6,439,232 to Brain. These were all basically designed by adding a second esophageal tube, ending at the supraglottic mask distal cuff tip. This second tube is usually molded by a semi rigid open ring, inside the body of the pneumatic cuff of the mask. This construction, when all is working well, allows the hollow orifice of the esophageal tube properly aligned with the esophageal entrance, so it could drain its content or allow a passage of an oro-gastric tube through it.

However for this device to work, proper insertion and positioning of the ventilation device (supraglottic mask) at the hypopharynx is critical. Its tip must be properly facing the esophageal entrance. If the mask is not in the right position, the proposed esophageal draining may not properly occur which may result in an increased risk of leakage of the esophageal/gastric contents. Any such contents may then be undesirably aspirated into the lungs with serious consequences. In order to accommodate an esophageal draining tube in addition to the tracheal tube, the thickness of this device is increased. The increased thickness may make proper insertion and installation of the device into the patient's throat more difficult.

Another device directed to reducing the risk of regurgitation and at the same time to provide for lung ventilation is disclosed in U.S. Pat. No. 5,499,625 by Frass. This is a twin lumen coaxial device designed for use in emergency situations and difficult airways. It can be inserted blindly into the oropharynx and usually enters the esophagus in about 90% of times. It has a low volume inflatable distal cuff and a much larger proximal pharyngeal cuff designed to completely occlude the oropharynx and the nasopharynx. It provides effective lung ventilation regardless of whether esophageal or tracheal placement is accomplished. When it is placed in the trachea, it functions as an endotracheal tube, with the distal cuff sealing the tube against the tracheal wall. When its distal cuff is in the esophagus, ventilation is possible through a second lumen that ends at perforations at the pharyngeal side of the tube above the lower cuff that occludes the esophagus and below the upper pharyngeal cuff. Due to its design, this device is limited to unconscious patients over 5 ft of height. Furthermore, an operator needs to be aware of symptoms to assure proper placement. If auscultation of breath sounds are negative and gastric insufflation is positive, the operator needs to immediately switch the lumen to provide air into the alternate airway. Its positioning is critical, as the airway could be occluded if not properly placed and the proper lumen is not used.

U.S. Pat. No. 4,995,388 to Archibald I. Brain discloses a larynx mask with a drain tube intruding into the esophagus and with an esophageal sealing cuff. In this device, the inflation line leads to the pharynx cuff and then serially down to the esophageal cuff.

U.S. Pat. Nos. 5,241,956; 5,355,879; 5,632,271; and 5,878,745 to Archibald Brain disclose a respective larynx mask with two inflatable seals for sealing about the pharynx. The seals may be inflated by a common inflation line or by separate inflation lines.

What is needed is a supraglottic mask with an esophageal drain tube and esophageal cuff in combination with an improved seal on the pharynx cuff, an improved pressure indicator, and an improved method of installation that will quickly form an esophageal obturator to reduce risk of choking on gastrointestinal contents.

SUMMARY OF THE DISCLOSURE

In accordance with one aspect of the invention, a supraglottic mask for an artificial airway device includes an inflatable supraglottic cuff having a peripheral seal with bellow shaped walls for inflating to a wedge shape. The bellow shaped walls have a plurality of bellow creases that fan out from an interior apex section when inflated to provide the inflated wedge shape from the interior apex section to a proximal wide section. The inflatable supraglottic cuff is connectable to air pressure lumen for control of inflation and deflation of the bellow shaped walls.

Preferably the supraglottic mask has a conduit with two separate tracheal and esophageal lumens laterally positioned adjacent each other with the tracheal lumen having an inlet within the confines of the peripheral seal and the esophageal lumen extending through an esophageal limb posteriority of the wedge in proximity to the apex section. It is desired that the posterior wall of the conduit is substantially flat to reduce rotation while positioned in the pharynx section of a patient.

It is also desired that the double lumen conduit has a substantially rectangular cross-sectional configuration with rounded corners for reducing its thickness. The bulkiness in the oro-pharyngeal cavity and hypopharynx is thus reduced, which in turn reduces the chances of trauma, although preserving its cross-sectional area to assure the proper flow of air to the trachea and for any eventual esophageal drainage.

It is further desired that an epiglottis band is attached near the wider or proximal border of the supraglottic cuff at an anterior section of the bellows for lateral extension and facing a laryngeal aperture to push forward and protect an epiglottis up to its natural flexed and opened position during the pneumatic expansion of the supraglottic cuff thereby reducing the risk of trauma to the epiglottis.

In one embodiment, the conduit has a reinforced ring located at the proximal segment thereof just before the conduit separates into a ventilation limb and esophageal limb for reducing damage and kinking of the double lumen tube when it passes through the mouth and teeth.

In accordance with another aspect of the invention, a combination artificial airway device and esophageal obturator includes a supraglottic inflatable cuff for installation above the esophageal opening at the oropharynx and the hypopharynx, and an esophageal inflatable cuff for installation in the esophagus. A tracheal lumen has an inlet within the peripheral seal formed by the supraglottic cuff. An esophageal drain lumen extends past the supraglottic inflatable cuff and through the esophageal cuff. An inflation line is serially connected to the esophageal cuff and then to the supraglottic cuff such that the inflating air supply passing through the inflation line passes to the esophageal cuff before passing to the supraglottic cuff.

It is preferred that a section of the inflation line passing from the esophageal cuff to the supraglottic cuff has more restriction than the inflation line leading to the esophageal cuff thereby promoting inflation of the esophageal cuff before inflation of the supraglottic cuff during normal inflation rates, such that the esophagus is isolated and previously sealed by the inflated esophageal cuff before the supraglottic cuff assumes its final inflated and sealing position.

It is further desired that the supraglottic cuff has its peripheral seal formed from bellow shaped walls for inflating to a wedge shape. The bellow shaped walls have a plurality of pleats or folds that fan out from an interior apex section when inflated to provide the inflated wedge shape from the interior apex section to a proximal wide section.

In accordance with another aspect of the invention, a combination artificial airway device and esophageal obturator includes a supraglottic inflatable cuff for installation above the esophageal sphincter or opening at the oropharynx and hypopharynx, and an esophageal inflatable cuff for installation in the esophagus. A tracheal lumen has an inlet entrance within the confines of the supraglottic cuff and in communication with the tracheal passage of the patient.

An esophageal lumen extends past the supraglottic inflatable cuff and through the esophageal cuff. An inflation line is for inflating both the esophageal cuff and supraglottic cuff. The supraglottic cuff has an asymmetrical inflatable section that has a wider proximal section situated above the epiglottis with its distal thinner termination end situated over the esophageal sphincter or entrance just behind the larynx to provide increased stability by its two points of sustain fixation. The stability is assured by a firmly positioned terminal esophageal cuff inside the esophagus, and the second, or the proximal point, at the exterior segment of the asymmetrical supraglottic cuff secured in the oropharynx area and fixed externally to the peri-oral aperture. This stable two point security makes it possible, during its pneumatic expansion, to ergonomically embrace and seal the peri-laryngeal structures contour.

Preferably, the tracheal lumen and esophageal lumen are in a low profile double lumen tube with the lumens positioned laterally side by side. The tube has a substantially flat posterior wall. The posterior wall in one embodiment is directly abuttable with the posterior wall of the pharynx and hypopharynx thereby restraining the tubes rotation while providing a solid and also stable base for the supraglottic cuff expansion.

Preferably, the supraglottic inflatable cuff is designed to be inflated in sequence after the esophageal cuff is pressurized by an independent backward fed internal inflation-deflation tube originating from the esophageal cuff and draining to said supraglottic cuff.

It is also desired that the device has a slight "s" shape form with a downward inclination of its distal point to facilitate esophageal access and an upward inclination proximal to the supraglottic cuff to be compatible with the anatomy of the pharynx toward the mouth.

It is preferred that a pilot balloon is mounted in the inflation line. The balloon is made from an elastic material and is circumferentially surrounded by a semi-spiral cylinder made from a resilient spring material. As a result of the pilot balloon inflation, the spring expands and is calibrated to indicate the pressure in the inflation line and cuffs. The expansion of the pilot balloon is a result of its inflation. The pressure build up will force an increase in the semi-spiral cylinder diameter that can be calibrated in a scale reflecting the internal pressure in the inflation line and cuffs.

In accordance with another aspect of the invention, a pilot balloon is inserted in an inflation line leading to the sealing cuff and is circumscribed, i.e., circumferentially surrounded, by a semi-spiral cylinder made from a resilient spring like material. Its expansion is a result of expansion of the pilot balloon and is calibrated to indicate pressure in the inflation line. The semi-spiral cylinder has an increase in diameter and a free edge sliding over another wall section of said semi-spiral cylinder which has a scale thereon for continuously indicating the pressure in the sealing cuff.

In accordance with another aspect of the invention, a method of intubation of a patient includes inserting an artificial airway device and esophageal obturator through the mouth and pharynx of a patient and inserting its distal end into the esophagus of the patient such that an esophageal drain tube and esophageal cuff are positioned in the esophagus and a supraglottic cuff with a tracheal lumen is positioned above the esophageal entrance with the tracheal lumen in communication with the trachea of the patient. The method further includes inflating the esophageal cuff to seal off the esophagus and subsequently inflating the supraglottic cuff to provide a seal about the peri-laryngeal structures of the patient.

It is preferred that the method includes the supraglottic cuff being asymmetrically shaped such that when inflated, its proximal section is wider and positioned above the epiglottis and a narrow section is placed at the opening of the esophagus.

It is preferred that the epiglottis of the patient is retained in its normal open up position toward the anterior wall of the pharynx by a strap laterally extending across the supraglottic cuff between two inflatable side walls of the cuff.

BRIEF DESCRIPTION OF THE DRAWINGS

Reference now is made to the accompanying drawings in which.

DETAILED DESCRIPTION OF THE PREFERRED EMBODIMENT

Figure 1:
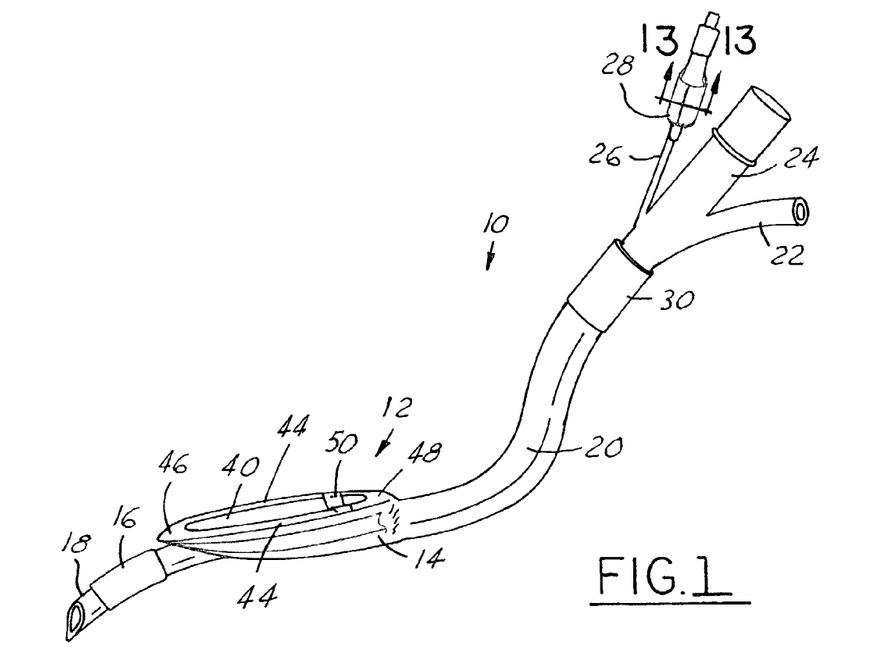
FIG. 1 is a perspective view of a larynx mask ventilation device

Referring now to FIGS. 1, a combination artificial airway device and esophageal obturator 10 includes a laryngeal mask 12 that has an inflatable supraglottic cuff 14. The device 10 also includes an inflatable esophageal cuff 16 near a distal end of an esophageal drain tube 18.

Figure 9:
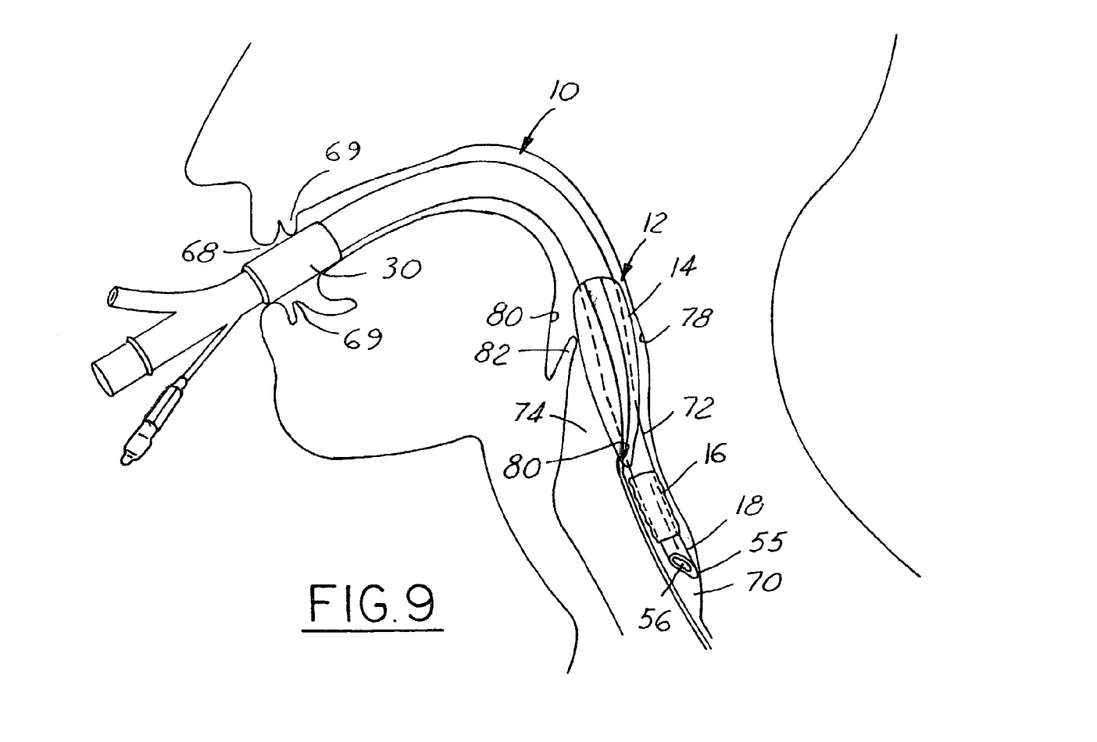
FIG. 9 is a diagrammatic and generally side elevational view shown in an initial position in a patient with both cuffs deflated.
Figure 10:
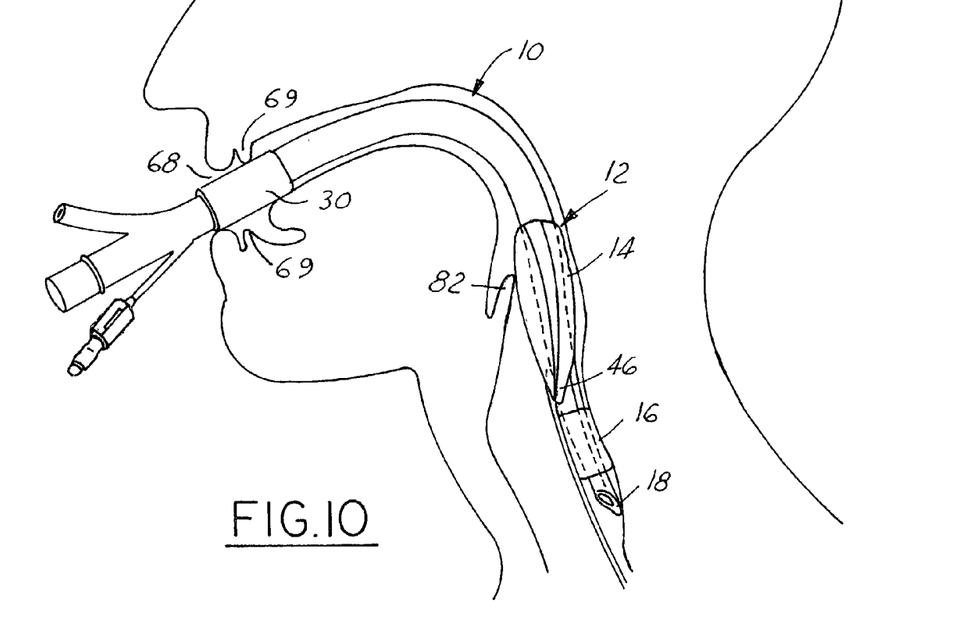
FIG. 10 is a view similar to FIG. 9 illustrating the esophageal cuff inflated in position.
Figure 11:
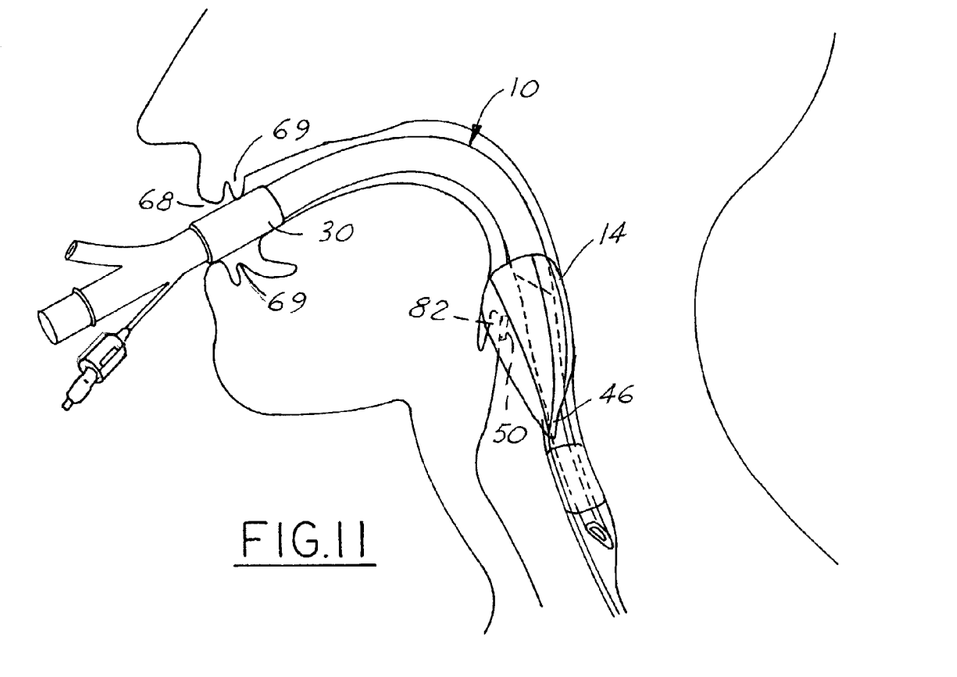
FIG. 11 is a view similar to FIG. 9 illustrating the device in a fully installed position with both the esophageal and supraglottic cuffs inflated.

The device 10 is shown in a resting position with a "S" like shape with the distal end of the drain tube 18 curved in a convex or upright direction as shown in FIGS. 9–11 and the conduit 20 curved in an opposite or concave direction, i.e. downward direction as shown in use in FIG. 9–11. of course, the device is flexible to allow proper handling and installation.

Figure 12:
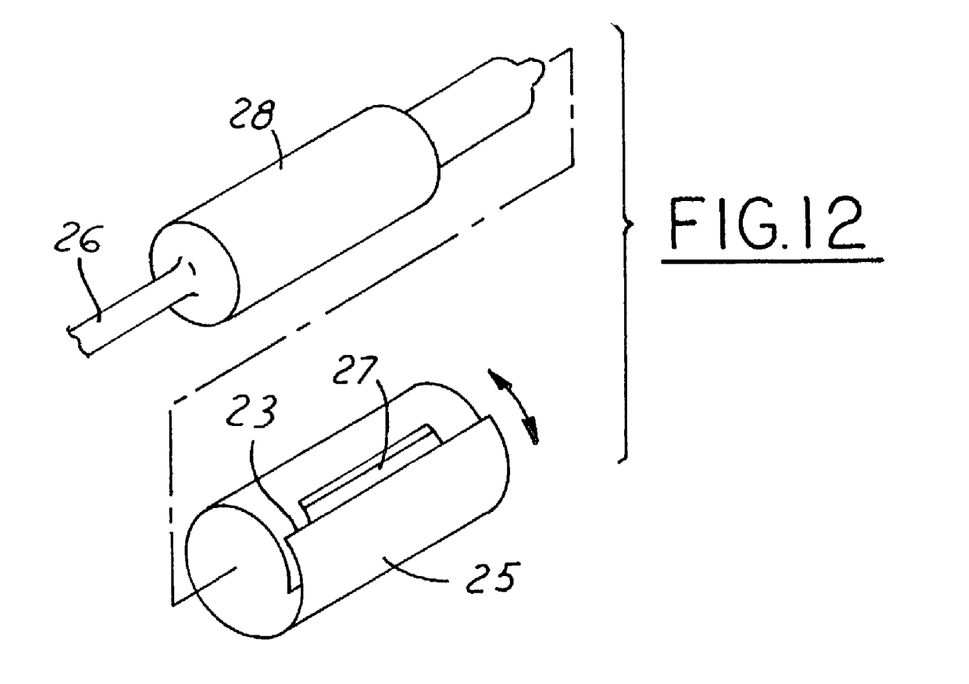
FIG. 12 is a enlarged fragmentary and exploded view of the pilot balloon shown in FIG. 1.
Figure 13:
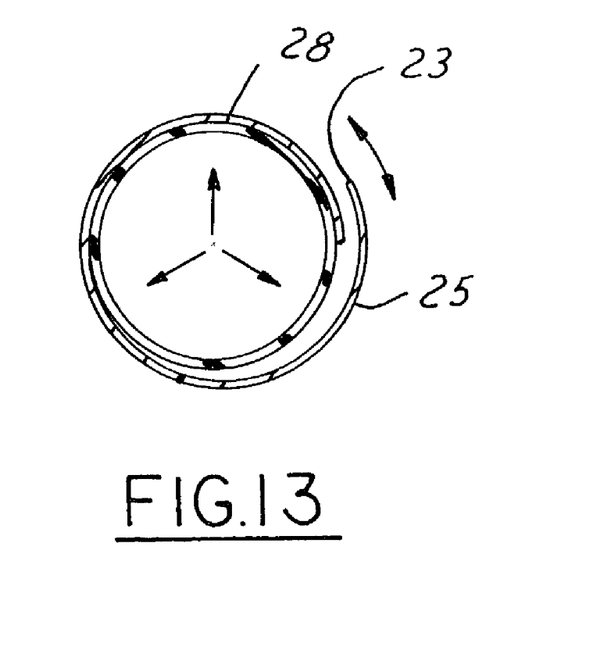
FIG. 13 is a cross-sectional view taken along lines 13—13 shown in FIG. 1.

The proximal end of conduit splits off into an esophageal limb 22, tracheal limb 24 and inflation limb or tube 26 with pilot balloon 28. The pilot balloon 28 can be made from an elastic material. As shown more clearly in FIGS. 12 and 13, the pilot balloon 28 is circumscribed or circumferentially surrounded by a semi-spiral cylinder 25 made from a resilient spring like material (thin metal or plastic) where its expansion, in consequence of the pilot balloon inflation, can be visualized and calibrated to indicate the internal pressure. It also will recoil, i.e., resiliently return to a normal rest position which corresponds to a deflated position of the pilot balloon. The expansion of this pilot balloon as a results of its inflation and a pressure built up, will force an increase in the semi spiral cylinder diameter that can be calibrated through a scale 27. The scale 27 may be a read text scale or a color scale, say "red" for over pressure or under pressure and "green" as a correct inflation pressure. The distal edge 23 of the spiral spring 25 lies over the under layer with the scale 27 thereon. By this way, monitoring and indicating of main cuff internal pressure is continuous during all times, reflecting its immediate inflation and deflation status. The pilot balloon 28 with scale 27 can then be used as an indicator of the proper inflation pressure inside the two main cuffs 14 and 16.

A reinforcing ring 30 is placed about conduit 20 just before the splitting off of limbs 22, 24 and 26. The proximal ends of limbs 22, 24, and 26 may have standard connectors well known in the art. Limb 24 may have for example a 15 mm male connector. Limb 26 may have for example a unidirectional valve and a syringe adaptor.

Figures 2, 3, 4:
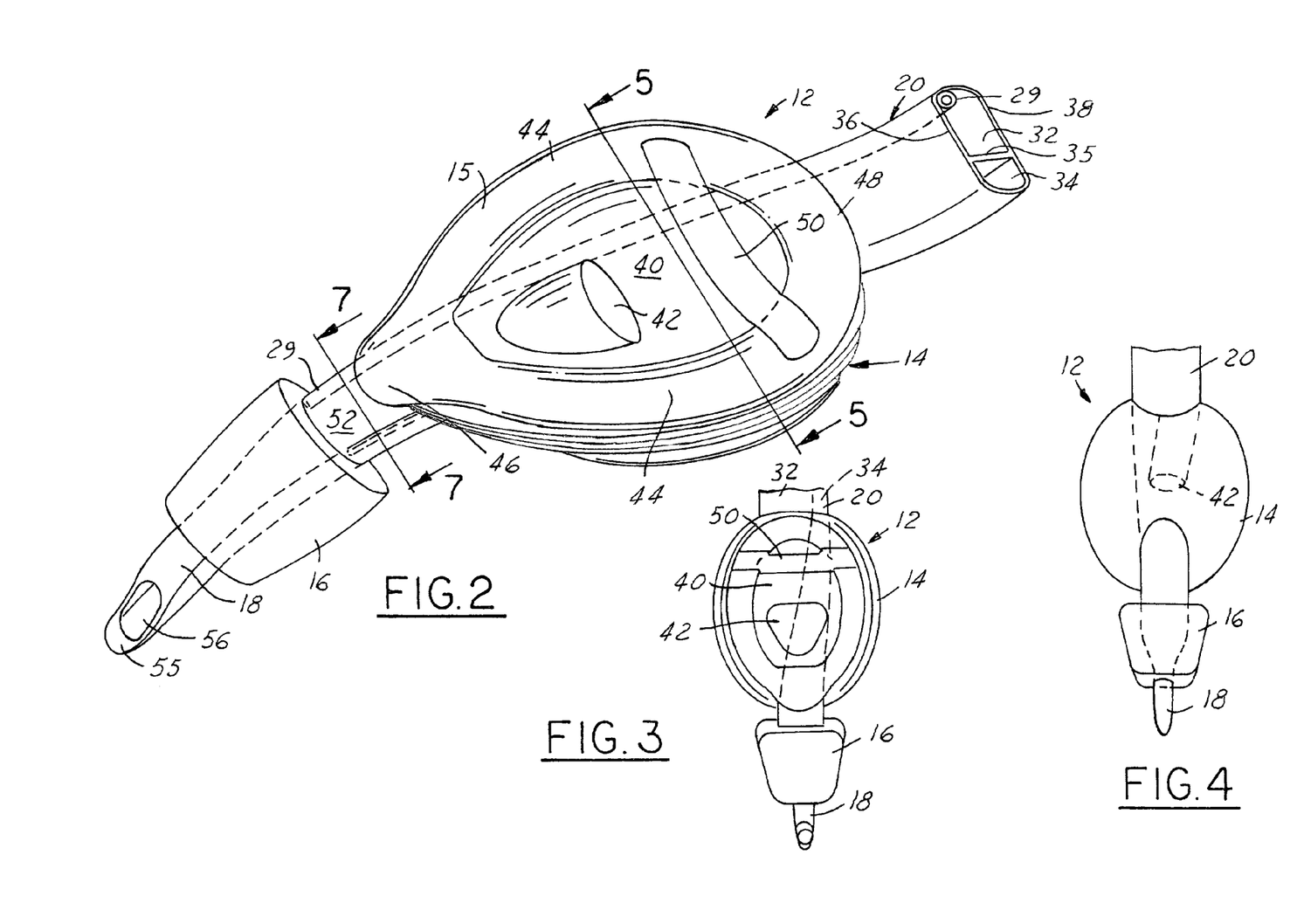
FIG. 2 is an enlarged fragmentary view illustrating the esophageal and supraglottic cuffs.
FIG. 3 is a front elevational view of the cuffs shown in FIG. 2.
FIG. 4 is a rear elevational view of the cuffs as shown in FIG. 2.

Referring now to FIGS. 2–4, the conduit 20 is a double lumen tube with a tracheal lumen 32, esophageal lumen 34 and inflation line 29 therein. Inflation line 29 is fluidly connected to inflation limb 26. Line 29 can be approximately 1 mm plastic tube for inflating and deflating the cuffs 14 and 16. The lumens 32 and 34 are laterally positioned from each other with a common dividing wall 35 therebetween. The conduit 20 has a flattened shape with relatively flat anterior wall 36 and posterior wall 38. Conduit 20 has a generally rectangular cross-section shape with rounded corners.

The mask 12 includes the supraglottic cuff 14 which provides a peripheral seal 15 that is substantially tear drop shaped or oval shaped about a concave front side with a center recess 40 that has an entrance 42 to the tracheal lumen 32. An epiglottic band 50 laterally extends across recess 40 and is attached to the two side walls 44 of the cuff in proximity to the proximal upper wall 48. The two side walls merge at a distal apex 46 section.

Figure 7:
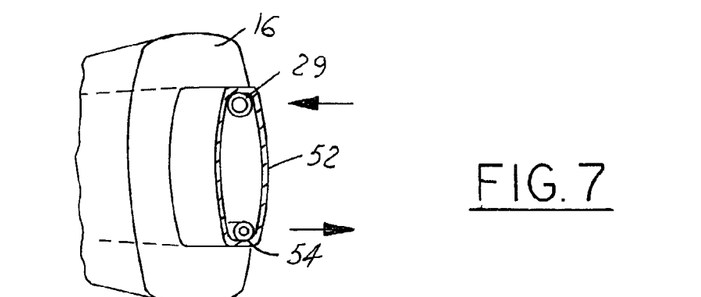
FIG. 7 is a cross sectional view taken along lines 7—7 shown in FIG. 2.

The apex section 46 of the supraglottic cuff is spaced from esophageal lumen 16 and connected thereby with an intermediate section 52 of conduit 20. This section 52 has lumen 34 therein along with inflation line 29 extending directly to esophageal cuff 16 and a restrictive line 54 that extends from the esophageal cuff 16 to the supraglottic cuff 14. The line 54 is significantly more restrictive than line 29 by having a substantially smaller diameter as clearly shown in FIG. 7. Intermediate line 54 connects directly to and forms part of the esophageal drain tube 18.

Esophageal cuff 16 is an annular inflatable bladder that inflates with air pressure introduced from line 29. The conduit line 54 of the drain tube 18 passes therethrough and is sufficiently rigid to not collapse under normal operating cuff pressures exerted on esophageal cuff 16. The distal end 55 of line 18 has a rounded duck bill shape, i.e. tapered shape, with drain opening 56 therein.

Air pressure can pass into line 54 to fill up supraglottic cuff 14. Conduit 20 is similarly sufficiently rigid to withstand collapse from normal inflation pressures exerted by inflated cuff 14.

Figure 5:
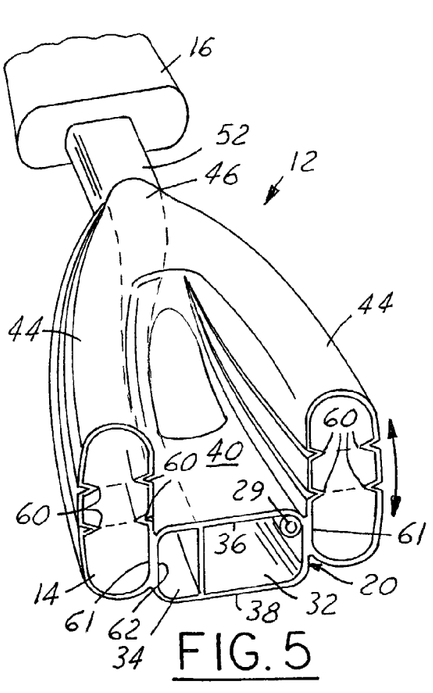
FIG. 5 is a cross-sectional view taken along lines 5—5 shown in FIG. 2.

As shown more clearly in FIG. 5, the side walls 44 are formed by bellows 60 which give the side walls an accordion like or pleated appearance. The bellows or pleats 60 merge near the apex 46 to provide more expansion or inflation near the proximal end 48. A portion 61 of side wall 44 is integral with side walls 62 of conduit 20. Side walls 44 are inflatable and thus expandable such that it forms a defined recess 40 on its concave side in front of the anterior wall 36 of conduit 20. The normal position of the bellows may be in the deflated state as shown in FIGS. 1 and 9 and may provide some resilient bias to the deflated position when inflated as shown in FIG. 5.

The conduit 30 has a substantially rectangular cross-sectional configuration with rounded corners. The posterior wall 38 is thus substantially flat in a lateral direction and forms a posterior wall that is abuttable against the posterior wall of the hypopharynx of the patient as shown in FIGS. 9–11.

Figure 6:
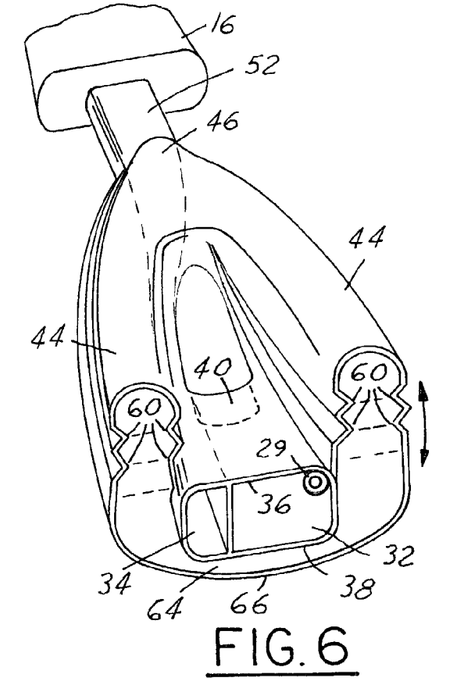
FIG. 6 is a view similar to FIG. 5 illustrating a modified embodiment.

Alternatively as shown in FIG. 6, a supraglottic cuff 14 may have the walls 44 extend to a posterior inflatable section 64 that is situated posteriorly of wall 38. In this embodiment, the posterior section has a posterior wall 66 that is spaced form wall 38 and is shaped to abut against the posterior walls of the hypopharynx section of the patient.

In operation, the device 10 is manually inserted through the mouth 68 of a patient as shown in FIG. 9 in a deflated condition. The distal end is directed through the esophageal sphincter 72 and into esophagus 70. The rounded duck bill end 55 of the drain tube section 18 and the "S" shape of the device promote entry into the esophagus 70. The rounded duck bill end 55 reduces trauma when it breaches through the esophageal sphincter.

The positioning of the device is easy because resistance is felt when the mask 14 apex portion 46 is lowered behind the arytenoid cartilage on the posterior wall of the supraglottic larynx. More particularly apex 46 is nested at the esophageal sphincter. Further insertion is then resisted which can be easily belt by the nurse, doctor or the operator. This increased resistance signals when to stop insertion and begin inflation through limb 26.

In this intruded position, the reinforced ring 30 is aligned with the teeth 69 within mouth 68 such that any pressure to close the conduit 20 and any of the lumens 32, 34 and inflation line 29 is successfully resisted by the structural support of the ring 30. It is also foreseen that the conduit material itself may be reinforced in this area to be structurally resistance against collapse.

Figure 8:
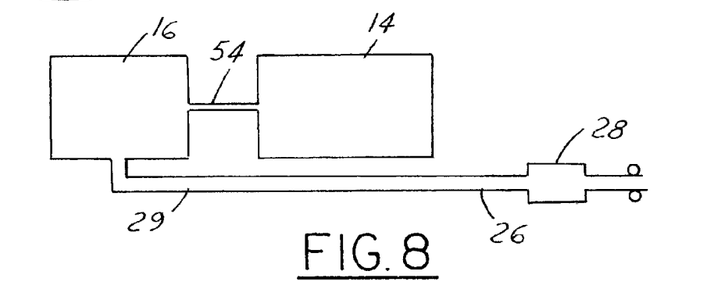
FIG. 8 is a schematic view illustrating the serial air path for sequentially inflating and deflating the esophageal and supraglottic cuffs.

As inflation proceeds through limb 26 the esophageal cuff 16 is the first cuff to inflate because line 29 proceeds directly to cuff 16. In other words line 29 bypasses cuff 14 and proceeds directly to cuff 16. The inflation of cuff 14 is also delayed because the line 54 that communicates from cuff 16 back to cuff 14 is restrictive which delays the inflation of cuff 14. The line 54 is small enough to delay the inflation of cuff 14 until cuff 16 if fully inflated during normal inflation rates for such devices 10. A schematic of the inflation lines is shown in FIG. 8 which schematically shows pilot 28, limb 26, line 29, esophageal cuff 14, restrictive line 54 and supraglottic cuff 14 serially connected.

It is also foreseen that other mechanism can be used to sequence the inflation of the cuffs 16 and 14 in the desired order. The material of cuff 16 may be more flexible and be slowed to inflate under less pressures than the materials used in cuff 14. Another alternative is that the bellows 60 may provide enough resilient resistance toward the deflated position against the inflation until the cuff 16 is fully inflated. The main point is that the device provides for a sequenced inflation of esophageal cuff 16 before the inflation of the cuff 14.

The advantage for the inflation of the esophageal cuff 16 is that by sequencing the inflation of the two cuffs provides for a faster inflation of the esophageal cuff 16 which provides faster protection against any potential regurgitation by the patient.

FIG. 10 shows the intermediate step when the esophageal cuff 16 is fully inflated but the cuff 14 is still in the deflated position. As shown as the cuff 16 is fully inflated, air is still passed through limb 26 and line 29 and now it flows through cuff 16 and back through line 54 to supraglottic cuff 16.

Referring now to FIG. 11, the cuff 16 inflates, the bellows expand to provide for the side walls and proximal wall 48 to increase width and form a seal about the tracheal entrance 74. The tracheal entrance 74 is sealed from the esophageal passage. The tracheal entrance is in communication with tracheal entrance 42 in the recess of the mask 12. The walls 44, 48 and apex provide for a complete seal by inflation which presses against the posterior wall 78 of the pharynx such that the inflated walls push against the anterior tissues 80 about the laryngeal entrance 74.

The bellows 60 provide for an inflated cuff that is asymmetrical in shape. Namely, a wedge or cone type shape is accomplished with the apex 46 near a narrow or thinner end and the wall 48 at the wider or thicker end. This wedge shape corresponds more closely with the natural shape of the patient's oro-pharynx and hypopharynx cavity. It is also foreseen that wall 48 may also be similarly bellowed or pleated like walls 44.

The laryngeal entrance is in communication with the concave side or recess 40 and the tracheal lumen entrance 42 which lead out to the tracheal limb 24.

The epiglottic band 50 is positioned and fixed on the side walls 44 to catch up with the epiglottis 82 and while the cuff 14 is inflating the band will push the epiglottis forward to its naturally open or flexed position as shown in FIG. 11. This reduces trauma to the epiglottis 82 and reduces complications in lung ventilation.

As can now be recognized, any gastric or esophageal reflux can then be drained through the tube 18 and lumen 34 out through limb 22. If necessary, an oro-gastric tube can be easily passed directly to the stomach through the esophageal limb 22, lumen 34 and entrance 56.

After the device is used and removal is desired, the limb 29 can be opened or a syringe can be used to deflate the two cuffs 14 and 16. The cuff 16 will deflate first and then the cuff 14 will deflate to allow quick removal from the esophagus.

In this fashion the supraglottic cuff 14 will pneumatically inflate and expand to seal the peri-laryngeal structures only after the esophagus is isolated and has been previously sealed by the inflated esophageal cuff 16. This assures the esophageal limb 22 a free pathway of any gastric-esophageal content to the exterior. Furthermore, a separate peripheral seal is formed about the peri-laryngeal mucosa adding an extra guarantee against any aspiration of gastro-esophageal contents. This seal also provides a clear way for the ventilation of the lungs.

The two cuffs, with a flat non-rotatable conduit provides for a stable intubation device less prone to undesirable displacement. The flat rectangular shaped conduit with the side by side double lumen structure positioned between the side inflatable walls 44 provide for a low profile mask 12 which can be easily inserted and then inflated to render proper sealing.

Furthermore, the asymmetrical ergonomic wedge or cone like shape of the inflated supraglottic mask provides for less intrusion and trauma to the surrounding tissues with the apex situated over the esophageal entrance or sphincter just behind the larynx and its wide end situated above the epiglottis. The band also provides for reduced trauma to the epiglottis.

The wedge like or cone like shape of the cuff allows the esophageal lumen to pass behind the mask 12 while still maintaining a low profile for easier insertion through the oral cavity and its passage throughout the oro-pharynx, hypo-pharynx and finally into the esophagus with reduced trauma of these structures.

The device may be made from an elastomeric silicone rubber or by other bio-compatible plastics in either a non-disposable and reusable format or in a disposable format.

The optional rear inflation section can provide even further pressure on the anterior wall of the hypo-pharynx to create increased forward pressure against the peri-laryngeal supraglottic structures and creating a tighter seal of the laryngeal entrance.

The reinforced ring provides for reduced damage and reduced risk of kinking of the double lumen conduit 20 when it passes through the mouth and teeth.

The continuous pressure monitor reduces the chance of overpressure and an over expansion of the cuffs which in turn may cause deleterious effects on the circulation (an increase in compression blocks or delays the mucous circulation). This increased intracuff pressure could lead to a higher incidence of sore throat pain or even necrosis, from the eventual ischemia and injury. Another reason to monitor the intracuff pressure besides to avoid its initial "overinflation" is, also when a ventilation device is used in anesthesia, and N2O (Nitrous Oxide) gas is added to oxygen (a common procedure to increase analgesia and reduce anesthetic consumption) this gas in time diffuses through the cuff walls to inside the cuff, it will also in time increase the intercuff pressure.

Furthermore, an underpressure due to inappropriate cuff inflation could also be deleterious as the proper contact between the cuff walls and the mucous surface may not occur. This could lead to leaks of air during the patient ventilation, resulting in not only inappropriate ventilation, but also an increased risk for lung aspiration of any eventual gastric content, in case of regurgitation, as the proper laryngeal seal is not achieved. The continuous monitoring by the pilot balloon provides an extra safeguard against these undesirable traumas.

Variations and modifications are possible without departing from the scope and spirit of the present invention as defined by the appended claims.

The invention claimed is:

1. A supraglottic mask for an artificial airway device, said mask comprising:
   an inflatable supraglottic cuff with peripheral seal having bellow shaped walls for inflating to a wedge shape;
   said bellow shaped walls having a plurality of bellow creases that fan out from a interior apex section when inflated to provide the inflated wedge shape from the interior apex section to a proximal wide section; and
   said inflatable cuff connectable to an air pressure lumen for control of inflation and deflation of the bellow shaped walls.

2. A supraglottic mask as defined in claim 1 further comprising:
   a conduit having two separate tracheal and esophageal lumens laterally positioned adjacent each other with the tracheal lumen having an inlet within the peripheral seal and the esophageal lumen extending through a esophageal limb posterior of the wedge in proximity to the apex section.

3. A supraglottic mask as defined in claim 2 further comprising:
   a posterior wall of said conduit being substantially flat to reduce rotation while positioned in said pharynx section of a patient.

4. A supraglottic mask as defined in claim 2 further comprising:
   an epiglottis band being attached near the wider or proximal border of the supraglottic cuff at an anterior section of the bellows for lateral extension and facing a laryngeal aperture to push forward and protect an epiglottis up to its natural flexed and opened position during the pneumatic expansion of the supraglottic cuff thereby reducing the risk of trauma to the epiglottis.

5. A supraglottic mask as defined in claim 4 further comprising:
   said conduit having a reinforced ring being located at a proximal segment thereof just before said conduit separates into a ventilation limb and esophageal limb for reducing damage and kinking of the double lumen tube when it passes through the mouth and teeth of a patient.

6. A combination artificial airway device and esophageal obturator comprising:
   a supraglottic inflatable cuff for installation above an esophageal entrance at a hypopharynx;
   an esophageal inflatable cuff for installation in an esophagus;
   a tracheal lumen having an inlet within a seal formed by the supraglottic cuff;
   an esophageal lumen extending past the supraglottic inflatable cuff and through the esophageal cuff; and
   an inflation line serially connected to the esophageal cuff and then to the supraglottic cuff such that the inflating air supply passing through the inflation line passes to the esophageal cuff before passing to the supraglottic cuff.

7. A combination artificial airway device and esophageal obturator as defined in claim 6 further comprising:
   a section of the inflation line passing from the esophageal cuff to the supraglottic cuff having more restriction than the line leading to the esophageal cuff thereby promoting inflation of the esophageal cuff before inflation of the supraglottic cuff during normal inflation rates, such that the esophagus is isolated and previously sealed by the inflated esophageal cuff before the supraglottic cuff assumes its final inflated position.

8. A combination artificial airway device and esophageal obturator as defined in claim 7 further comprising:
   said supraglottic cuff having a peripheral seal having bellow shaped walls for inflating to a wedge shape; and
   said bellow shaped walls having a plurality of bellow creases that fan out from a interior apex section when inflated to provide the inflated wedge shape from the interior apex section to a proximal wide section.

9. A combination artificial airway device and esophageal obturator comprising:
   a supraglottic inflatable cuff for being installable above a larynx;
   an esophageal inflatable cuff for being installable in an esophagus;
   a tracheal lumen having an inlet within the confines of the supraglottic cuff;
   an esophageal lumen extending past the supraglottic inflatable cuff and through the esophageal cuff; and
   an inflation line for inflating both the esophageal cuff and supraglottic cuff; and
   said supraglottic cuff having an asymmetrical inflatable section that has a wider proximal section for being positionable above an epiglottis with its distal thinner termination end being positionable over an esophageal entrance just behind a larynx wherein a stable support base is achieved to provide increased stability for the inflation of said supraglottic cuff by having two points of sustain fixation with a first point by a firmly positioned terminal esophageal limb positionable inside an esophagus, and the second, or the proximal point, by an exterior segment of an asymmetrical conduit securable in an oropharynx area and fixable externally to a peri-oral aperture, making during the pneumatic expansion of said supraglottic cuff, it embraceable and sealable to a peri-laryngeal structural contour.

10. A combination artificial airway device and esophageal obturator as defined in claim 9 further comprising said conduit including:

said tracheal lumen and esophageal lumen in a low profile double lumen tube with said lumens positioned laterally side by side and having a substantially flat posterior wall; and said posterior wall is directly abuttable with the posterior wall of an oro-pharynx and a hypopharynx, restraining its rotation while providing a solid and also stable base for the supraglottic cuff expansion.

11. A combination artificial airway device and esophageal obturator as defined in claim 10 further comprising:

said supraglottic inflatable cuff designed to being inflated in sequence after the esophageal cuff is pressurized, by an independent backward fed internal inflation-deflation tube originating from the esophageal cuff and draining to said supraglottic cuff.

12. A combination artificial airway device and esophageal obturator as defined in claim 11 further comprising:

the device has an "s" shape form with a downward inclination of its distal point to facilitate its access to an esophagus and an upward inclination proximal to the supraglottic cuff to be compatible with the anatomy of a pharynx toward a mouth.

13. A combination artificial airway device and esophageal obturator as defined in claim 12 further comprising:

the double lumen tube being asymmetrical with a substantially rectangular cross-sectional configuration with rounded corners whereby its thickness and bulkiness is reduced in an oro-pharyngeal cavity and hypopharynx, which in turn diminishes the chances of trauma, although preserving its cross-sectional area to assure the proper flow of air to the trachea and to any esophageal drainage, said tracheal lumen being larger than said esophageal lumen.

14. A combination artificial airway device and esophageal obturator as defined in claim 13 further comprising:

a pilot balloon mounted in the inflation line and being made from an elastic material that is circumferentially surrounded by a semi-spiral cylinder made from a resilient spring material which can be expanded, as a result of the pilot balloon inflation providing a visual acceptable or unacceptable indication of the pressure in the inflation line and cuffs, and the expansion of the pilot balloon as a result of its inflation and pressure built up, will force an increase in the semi spiral cylinder diameter that could be graphically marked to visually indicate an acceptable range of the internal pressure in the inflation line and cuffs.

15. A method of intubation of a patient comprising:

inserting a double lumen artificial airway device and esophageal obturator through the mouth and pharynx of a patient and inserting its distal end into the esophagus of a patient such that an esophageal drain tube and esophageal cuff are positioned into an esophagus and a supraglottic cuff with a tracheal lumen is positioned in a hypopharynx over a larynx above the esophageal entrance with the tracheal lumen in communication with the trachea of the patient;

inflating the esophageal cuff to seal off an esophagus and isolate access of an esophagus only through said esophageal drain tube; and subsquentially inflating the supraglottic cuff to provide a seal about the peri-laryngeal structures of the patient.

16. A method of intubation as defined in claim 15 further comprising:

said supraglottic cuff being asymmetrically shaped such that when inflated, its proximal section is wider and positioned above an epiglottis and a its distal narrow section is placed at the entrance of an esophagus.

17. A method of intubation as defined in claim 16 further comprising:

retaining the epiglottis of a patient against the anterior wall of a pharynx by a strap laterally extending across the supraglottic cuff between two inflatable side walls of the cuff.

18. A method of intubation as defined in claim 15 further comprising:

said inflating of the esophageal cuff and said subsequent inflating of the supraglottic cuff being done through a single inflation line serially connected to the esophageal cuff and then restrictively to the supraglottic cuff.

19. A method of intubation of a patient comprising:

inserting an artificial airway device and esophageal obturator through a mouth and pharynx of a patient and inserting its distal end into an esophagus of the patient such that an esophageal drain tube and esophageal cuff are positioned into an esophagus and a supraglottic cuff with a tracheal lumen is positioned in a hypopharynx over a larynx and above the esophageal entrance with the tracheal lumen in communication with a trachea of a patient;

inflating the esophageal cuff to seal off the esophagus;

subsequently inflating the supraglottic cuff to provide a seal about the peri-laryngeal structures of a patient;

said supraglottic cuff being asymmetrically shaped such that when inflated, its proximal section is wider and positioned above an epiglottis and its distal narrow section is placed at the entrance of an esophagus; and retaining the epiglottis of a patient against the anterior wall of a pharynx by a strap laterally extending across the supraglottic cuff between two inflatable side walls of the cuff.

20. A method of intubation of a patient comprising:

inserting an artificial airway device and esophageal obturator through the mouth and pharynx of a patient and inserting its distal end into the esophagus of the patient such that an esophageal cuff is positioned into an esophagus and a supraglottic cuff with a tracheal lumen is positioned in a hypopharynx over a larynx and above the esophageal entrance with the tracheal lumen in communication with the trachea of a patient;

inflating the esophageal cuff through a pressure line that is serially connected to the esophageal cuff and the supraglottic cuff to seal off the esophagus; and subsequently inflating the supraglottic cuff through the same pressure line to provide a seal about the peri-laryngeal structures of a patient.

* * * * *